United States Patent
Kreft et al.

(10) Patent No.: US 11,305,211 B2
(45) Date of Patent: Apr. 19, 2022

(54) CONDENSATE SEPARATOR FOR EXHAUST GAS MEASURING SYSTEMS

(71) Applicant: AVL EMISSION TEST SYSTEMS GMBH, Neuss (DE)

(72) Inventors: Norbert Kreft, Meerbusch (DE); Christopher Garthe, Kaarst (DE); Torsten Bornemann, Willich (DE); Dirk Woiki, Duesseldorf (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 352 days.

(21) Appl. No.: 16/476,078

(22) PCT Filed: Dec. 1, 2017

(86) PCT No.: PCT/EP2017/081200
§ 371 (c)(1),
(2) Date: Jul. 4, 2019

(87) PCT Pub. No.: WO2018/127331
PCT Pub. Date: Jul. 12, 2018

(65) Prior Publication Data
US 2019/0344197 A1     Nov. 14, 2019

(30) Foreign Application Priority Data
Jan. 6, 2017  (DE) ..................... 10 2017 100 180.8

(51) Int. Cl.
*B01D 5/00*    (2006.01)
*B01D 53/26*    (2006.01)
*G01N 33/00*    (2006.01)

(52) U.S. Cl.
CPC ............ *B01D 5/009* (2013.01); *B01D 53/265* (2013.01); *G01N 33/0014* (2013.01); *B01D 2257/80* (2013.01)

(58) Field of Classification Search
None
See application file for complete search history.

(56) References Cited

U.S. PATENT DOCUMENTS

| 2,187,646 A | 1/1940 | Darrietis |
| 2,726,732 A | 12/1955 | Faust et al. |
| (Continued) |

FOREIGN PATENT DOCUMENTS

| CN | 2039390 U | 6/1989 |
| CN | 201955264 U | 8/2011 |
| (Continued) |

OTHER PUBLICATIONS

Translation of DE3706941A1, accessed Aug. 23, 2021 (Year: 1988).*
Translation of DE1769579A1, accessed Aug. 23, 2021 (Year: 1971).*

*Primary Examiner* — Frank M Lawrence, Jr.
*Assistant Examiner* — Phillip Y Shao
(74) *Attorney, Agent, or Firm* — Norman B. Thot

(57) ABSTRACT

A condensate separator for an exhaust gas measuring system. The condensate separator includes a housing with condensate discharge opening, an inlet opening arranged in the housing, a cooled inlet line which introduces a fluid into the housing, and a gas outlet port with a gas entrance and a gas exit. The cooled inlet line opens into the inlet opening. The gas outlet port opens into a gas outlet line. A cross-sectional area of the gas entrance of the gas outlet port is larger than a cross-sectional area of the gas exit of the gas outlet port.

8 Claims, 2 Drawing Sheets

(56) References Cited

U.S. PATENT DOCUMENTS

| | | | |
|---|---|---|---|
| 3,200,568 A * | 8/1965 | McNeil | B07B 7/08 |
| | | | 96/195 |
| 3,529,405 A | 9/1970 | Ashbrook | |
| 4,755,194 A | 7/1988 | Rooker et al. | |
| 5,466,270 A | 11/1995 | Abdelmalek | |
| 5,820,641 A * | 10/1998 | Gu | B01D 5/0036 |
| | | | 55/434.4 |
| 6,129,775 A * | 10/2000 | Conrad | A47L 9/1608 |
| | | | 55/337 |
| 2006/0130653 A1 | 6/2006 | Balingit | |
| 2007/0163442 A1 * | 7/2007 | Saito | B04C 5/13 |
| | | | 96/209 |
| 2008/0034784 A1 | 2/2008 | Schillemeit et al. | |
| 2012/0297986 A1 * | 11/2012 | Suda | B04C 5/103 |
| | | | 96/212 |
| 2015/0174508 A1 * | 6/2015 | Bozic | B01D 46/2411 |
| | | | 210/188 |
| 2016/0082366 A1 * | 3/2016 | Yang | B01D 19/0052 |
| | | | 96/216 |

FOREIGN PATENT DOCUMENTS

| | | | |
|---|---|---|---|
| CN | 103471878 A | 12/2013 | |
| CN | 203862086 U | 10/2014 | |
| DE | 17 69 579 A1 | 10/1971 | |
| DE | 74 13 770 U | 7/1974 | |
| DE | 37 06 941 A1 | 9/1988 | |
| EP | 0 291 630 A2 | 11/1988 | |
| FR | 2 581 892 A1 | 11/1986 | |
| JP | 2001-4503 A | 1/2001 | |
| JP | 2005-233890 A | 9/2005 | |
| JP | 2006-177717 A | 7/2006 | |

\* cited by examiner

CONDENSATE SEPARATOR FOR EXHAUST GAS MEASURING SYSTEMS

CROSS REFERENCE TO PRIOR APPLICATIONS

This application is a U.S. National Phase application under 35 U.S.C. § 371 of International Application No. PCT/EP2017/081200, filed on Dec. 1, 2017 and which claims benefit to German Patent Application No. 10 2017 100 180.8, filed on Jan. 6, 2017. The International Application was published in German on Jul. 12, 2018 as WO 2018/127331 A1 under PCT Article 21(2).

FIELD

The present invention relates to a condensate separator for an exhaust gas measuring system comprising a housing with a condensate discharge opening, a cooled inlet line for introducing a fluid into the housing, wherein the inlet line opens into an inlet opening arranged in the housing, and a gas outlet port comprising a gas entrance and a gas exit, wherein the gas outlet port opens into a gas outlet line.

BACKGROUND

Condensate separators have previously been described and serve to separate water from fluids, in particular from gases or gas mixtures. Condensate separators are used in exhaust gas measuring systems to separate water from sample gas flows containing exhaust gases with water or water vapor. During the combustion of fuels, water vapor is produced which is contained as a component in the exhaust gas flow, wherein the fluid is just saturated with water vapor at the dew point. If the temperature of the fluid is decreased below the dew point, the water vapor condenses and the condensate is in the liquid phase. Such a condensation in the measuring device can, for example, cause incorrect results from spectroscopically working measuring devices. The aggregates of the exhaust gas measuring systems can be contaminated so that the life span of the measuring devices is reduced, for example, due to corrosion.

The reduction of the fluid temperature below the dew point is therefore used to specifically reduce the content of water vapor in the exhaust gas and to separate the condensate before the measuring device in order to dry the sample gas. The sample gas is directed through a cooler into a condensate separator therefor, where the condensate is separated from the fluid, and the separated condensate is then directed into a condensate tank from which the condensate is discharged at intervals or continuously via a discharge valve.

DE 37 06 941 A1 describes a device for cooling gases. The cooler comprises a tank filled with a cooling liquid. An inlet line passes through the tank filled with the cooling liquid, wherein the inlet line opens into a condensate separator and flows through the fluid to be cooled. The condensate separator comprises a cylindrical section and an adjacent conical section, wherein the conical section is tapered downwards and opens into a condensate discharge opening. An immersion tube, which is used as a gas outlet port and which opens into a gas discharge line, immerses into the condensate separator at the end of the condensate separator opposite to the condensate discharge opening, wherein the gas dried by the condensate separation flows out of the condensate separator through the immersion tube.

A disadvantage of the embodiment described in DE 37 06 941 A1 is that the gas volume flow flowing off through the gas outlet port entrains already separated condensate as a result of the high flow speed of the gas volume flow and thus transports the condensate through the immersion tube from the condensate separator to the measuring devices.

SUMMARY

An aspect of the present invention is to further develop a condensate separator so that the separated condensate is not entrained by the gas volume flow to the measuring devices.

In an embodiment, the present invention provides a condensate separator for an exhaust gas measuring system. The condensate separator includes a housing comprising a condensate discharge opening, an inlet opening arranged in the housing, a cooled inlet line configured to introduce a fluid into the housing, and a gas outlet port comprising a gas entrance and a gas exit. The cooled inlet line is arranged to open into the inlet opening. The gas outlet port is arranged to open into a gas outlet line. A cross sectional area of the gas entrance of the gas outlet port is larger than a cross sectional area of the gas exit of the gas outlet port.

BRIEF DESCRIPTION OF THE DRAWINGS

The present invention is described in greater detail below on the basis of embodiments and of the drawings in which.

DETAILED DESCRIPTION

Figure 1:
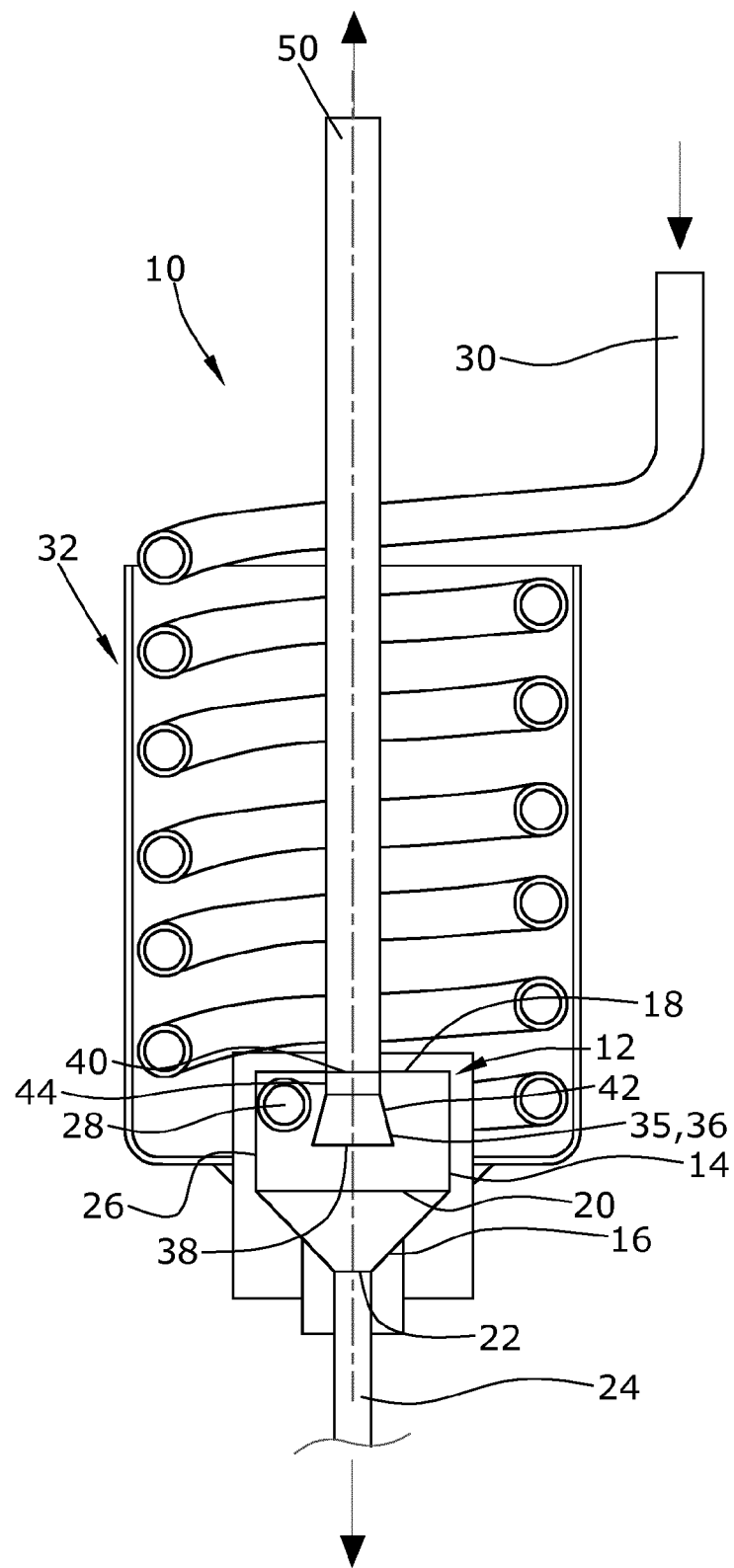
FIG. 1 shows an embodiment of the gas outlet port of the condensate separator of the present invention.

Since the cross-sectional area of the gas entrance of the gas outlet port is larger than the cross-sectional area of the gas exit of the gas outlet port, the flow speed of the gas volume flow is reduced at the gas entrance of the gas outlet port, thereby preventing the entrainment of condensate by the gas volume flow to the gas outlet port and to the measuring devices in a simple a cost-effective way.

In an embodiment of the present invention, the inlet opening can, for example, be arranged on a side wall of the housing, wherein the inlet line tangentially opens into the housing and the fluid is introduced tangentially into the housing. The housing can, for example, be cylindrical. The tangential introduction of the fluid directs the fluid into a circular path, wherein the condensate is centrifuged outwards by the centrifugal force acting thereon onto the side wall of the condensate separator, is decelerated on the side wall of the condensate separator and adheres thereon so that the condensate is separated from the fluid volume flow. The separated condensate flows along the side wall of the condensate separator down to the condensate discharge opening. The gas dried in this way flows off through the gas outlet port from the condensate separator. The condensate is thus separated from the fluid in a simple and cost-effective way.

In an embodiment of the present invention, the gas outlet port can, for example, comprise a conical section between the gas entrance and the gas exit, whereby the dead volume occurring with an unsteady cross-sectional transition is avoided. By avoiding the dead volume in the gas outlet port, the gas lines in the exhaust gas measuring system can be reduced in size and the exhaust gas volume flow required for the measurements can be reduced.

In an embodiment of the present invention, the gas outlet port can, for example, comprise a dimensional deviation between the gas entrance of the gas outlet port and the gas exit of the gas outlet port. The cross-sectional change between the gas exit of the gas outlet port and the gas entrance can be easily provided thereby.

In an embodiment of the present invention, the gas outlet port can, for example, be adapted as an immersion tube immersing into the housing and thus fulfilling the function of a static classifier.

In an embodiment of the present invention, the gas entrance of the immersion tube, viewed in the direction of the symmetry axis of the housing, can, for example, be arranged between the inlet opening and the condensate discharge opening, thereby avoiding a short circuit between the inlet opening and the outlet opening due to which the fluid could directly flow into the immersion tube prior to the condensate separation. The fluid flowing into the housing must thus first circulate along the cylinder wall of the housing before it can flow into the immersion tube.

In an embodiment of the present invention, the immersion tube can, for example, concentrically immerse into the housing so that the flow to the gas exit does not influence the tangential flow in the condensate separator. A sufficient distance to the ground is also maintained when using a conical outlet area of the condensate separator.

In an embodiment of the present invention, the gas outlet port can, for example, extend outwards from an upper base surface of the housing. The gas outlet port can thus already be produced in the production process of the housing, thereby reducing manufacturing and installation costs.

In an embodiment of the present invention, the cross sectional area of the gas entrance can, for example, be twice as large as the cross sectional area of the gas exit. Due to such a ratio of the cross sectional area of the gas entrance of the gas outlet port and the gas exit to each other, particularly little condensate that has already been separated is entrained by the gas volume flow into the gas outlet port.

In an embodiment of the present invention, the inlet line can, for example, helically pass through the cooler. The fluid thereby cools down in the cooler and the water vapor contained in the fluid condenses, wherein the condensate is entrained by the fluid flow. Since the inlet line is adapted helically, more heat can be dissipated from the fluid as a larger surface of the inlet line is surrounded by the cooling medium.

In an embodiment of the present invention, the diameter of the inlet line can, for example, correspond at least to the diameter of a condensing droplet of the condensate. The fluid volume flow generated by a pump is thereby always provided, wherein the blocking of the inlet line and a pressurization in the inlet line caused by the condensate is prevented.

In an embodiment of the present invention, the housing can, for example, comprise a cylindrical housing section which is provided with the inlet opening and a conical housing section that is adjacent the cylindrical housing section and which is provided with the condensate discharge opening. In the cylindrical housing section, the fluid is introduced into the condensate separator and directed to a cylindrical path. In the conical housing section adjacent to the cylindrical housing section, the flow speed of the fluid and thus the centrifugal force acting on the condensate are increased, thereby increasing the amount of condensate separated from the fluid. It is thus avoided that condensate drops from the inlet opening onto a smooth surface of the housing below the inlet opening which could cause splash water that could be entrained to the gas exit.

A condensate separator for exhaust gas measuring systems is thus provided that prevents, in a simple and cost-effective way, that the separated condensate is entrained by the gas volume flow to the gas outlet port, thereby preventing contamination of measuring devices, measurement inaccuracies in measurements, and corrosion-related failures of measuring devices.

Exemplary embodiments of a condensate separator for exhaust gas measuring systems according to the present invention are shown in the drawings and are described below.

FIG. 1 shows a condensate separator 10 for an exhaust gas measuring system comprising a housing 12 having a cylindrical housing section 14 and a conical housing section 16. The cylindrical housing section 14 comprises a closed upper base surface 18 and an open lower base surface 20, wherein the conical housing section 16 is adjacent to the open lower housing surface 20. The conical housing section 16 is tapered downwards so that the diameter of the conical housing section 16 reduces from the open lower base surface 20 of the cylindrical housing section 14 to a condensate discharge opening 22 arranged at the lower end of the conical housing section 16. An outflow line 24 adjacent to the condensate discharge opening 22 connects the condensate separator 10 to, for example, a condensate collecting tray (which is not shown in the drawings).

The circumferential side wall 26 of the cylindrical housing section 14 is provided with an inlet opening 28 connected to an inlet line 30, wherein the inlet line 30 is helically adapted and passes through a cooler 32.

An immersion tube 36 connected to the gas outlet line 50 immerses through the closed upper base surface 18 of the cylindrical housing section 14 into the housing 12, wherein said immersion tube 36 is adapted as a gas outlet port 35. The immersion tube 36 comprises a gas entrance 38 arranged in the housing 12 and a gas exit 40 arranged in the horizontal plane of the closed upper base surface 18 of the cylindrical housing section 14 and directed towards the gas outlet line 50.

According to the present invention, the cross-sectional area of the gas entrance of the immersion tube 36 and of the gas outlet port 35, respectively, is larger than the cross-sectional area of the gas exit 40 of the immersion tube 36 and of the gas outlet port 35, respectively. For the cross-sectional change between the gas entrance 38 and the gas exit 40, the immersion tube 36 comprises conical section 42 adjacent to a cylindrical section 44. The immersion tube 36 is arranged to be fixed via the cylindrical section 44 on the closed upper base surface 18 of the cylindrical housing section 14 and immerses with the cylindrical section 44 into the housing 12. The conical section 42 is adjacent to the cylindrical section 44 immersed into the housing 12, wherein the conical section 42 is tapered from the gas entrance 38 to the transition in the cylindrical section 44. The immersion tube 36 could alternatively comprise a dimensional deviation instead of the conical section 42.

Figure 2:
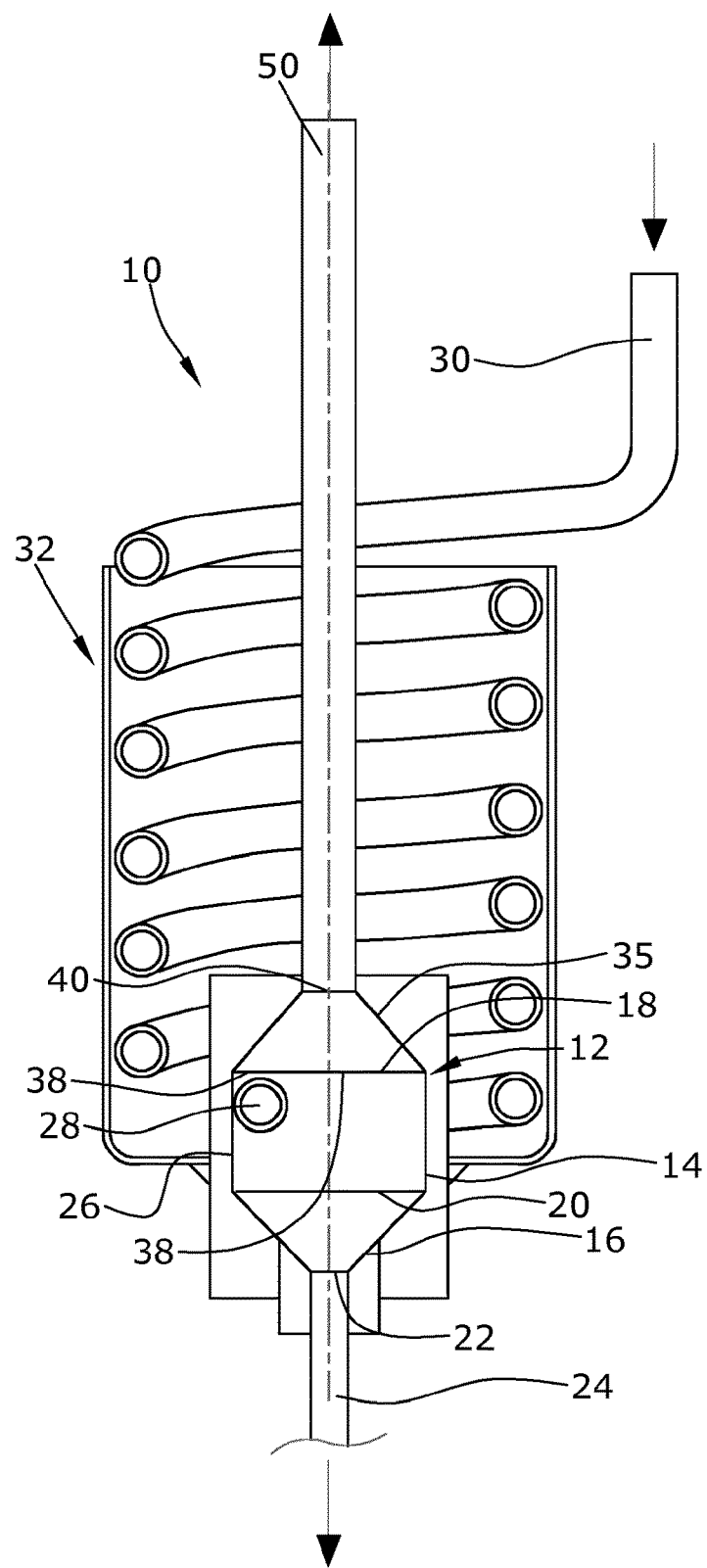
FIG. 2 shows an embodiment of the gas outlet port of the condensate separator of the present invention.

FIG. 2 shows a condensate separator 10 comprising a housing 12 having, as in FIG. 1, a cylindrical housing section 14 with an inlet opening 28 on the cylinder wall/circumferential side wall 26 of the cylindrical housing section 14, and having a conical housing section 16 with a condensate discharge opening 22. The cylindrical housing section 14 comprises a closed upper base surface 18 and an open lower base surface 20, wherein the conical housing section 16 is adjacent to the open lower base surface 20. The conical housing section 16 is tapered downwards and comprises the condensate discharge opening 22 at the lowest point.

In contrast to the embodiment shown in FIG. 1, the gas outlet port 35 does not immerse into the housing 12 but is adjacent to the upper base surface of the cylindrical housing section 14. The gas outlet port 35 comprises a gas entrance 38 and a gas exit 40 in fluid communication with a gas outlet line 50, wherein the diameter of the gas entrance 38 corresponds to the diameter of the closed upper base surface 18 of the cylindrical housing section 14 and is tapered from the closed upper base surface 18 to the gas exit 40 of the gas outlet port 35. The cross-sectional area of the gas entrance 38 is, according the present invention, larger than the cross-sectional area of the gas exit 40.

The separation process of the condensate is the same in both embodiments described in FIGS. 1 and 2. In the separation process of the condensate, the fluid first flows through the cooled inlet line 30 to the inlet opening 28. The inlet line 30 is cooled by the cooler 32, which is a pot-shaped tank filled with a cooling medium, through which the helically adapted inlet line 30 passes. The fluid is thereby cooled down below the temperature of the fluid, thereby condensing the water vapor contained in the fluid. The condensate is entrained by the volume flow of the fluid and transported to the housing 12. The fluid with the condensed condensate tangentially flows through the inlet opening 28 on the cylinder wall 26 to the housing 12, wherein the fluid and the condensate circulate along the cylinder wall 26 of the housing 12 due to the cylindrical form of the housing 12. Due to the higher mass of the condensate droplets, a higher centrifugal force acts on the condensate droplets, which causes the condensate droplets entrained by the volume flow of the fluid to be centrifuged out of the fluid onto the cylinder wall 26, to be decelerated at the cylinder wall 26, and to flow off via the cylinder wall 26 to the condensate discharge opening 22. An outflow line 24 adjacent to the condensate discharge opening 22 connects the condensate separator 10 to, for example, a condensate collecting tray (which is not shown in the drawings).

The conical housing section 16 of the housing 12 serves to increase the flow speed of the volume flow of the fluid, thereby again increasing the centrifugal force acting on the condensate droplets and thus the separation of the condensate.

The gas is thereby condensate-free and flows in the center of the housing 12 to the gas entrance 38 of the gas outlet port 35. The larger cross-sectional area of the gas entrance 38 compared to the gas exit 40 of the gas outlet port 35 causes a reduction in the flow speed of the gas volume flow at the gas entrance 38, thereby preventing the already separated condensate from being entrained by the gas volume flow into the gas outlet port 35.

A condensate separator for exhaust gas measuring systems is thus provided that prevents in a simple and cost-effective way already separated condensate from being entrained by the gas volume flow, thereby preventing s contamination of measuring devices, measurement inaccuracies in measurements, and corrosion-related failures of measuring devices.

It should be clear that the scope of protection of the present invention is not limited to the described exemplary embodiments. Reference should also be had to the appended claims.

What is claimed is:

1. A condensate separator for an exhaust gas measuring system, the condensate separator comprising:
   a housing comprising a condensate discharge opening and an upper base surface;
   an inlet opening arranged in the housing;
   a cooled inlet line configured to introduce a fluid into the housing, the cooled inlet line being arranged to open into the inlet opening; and
   a gas outlet port comprising a gas entrance and a gas exit, the gas outlet port being arranged to open into a gas outlet line and to extend outwards from the upper base surface of the housing,
   wherein,
   a cross sectional area of the gas entrance of the gas outlet port is larger than a cross sectional area of the gas exit of the gas outlet port.

2. The condensate separator as recited in claim 1, wherein, the housing further comprises a side wall,
   the inlet opening is arranged on the side wall of the housing, and the cooled inlet line is further configured to tangentially open into the housing.

3. The condensate separator as recited in claim 1, wherein the gas outlet port further comprises a conical section which is arranged between the gas entrance and the gas exit.

4. The condensate separator as recited in claim 1, wherein the cross sectional area of the gas entrance is twice as large as the cross sectional area of the gas exit.

5. The condensate separator as recited in claim 1, further comprising:
   a cooler,
   wherein,
   the cooled inlet line is arranged to helically pass through the cooler.

6. The condensate separator as recited in claim 1, wherein a diameter of the cooled inlet line corresponds at least to a diameter of a condensing droplet.

7. The condensate separator as recited in claim 1, wherein the housing further comprises,
   a cylindrical housing section which has the inlet opening arranged therein, and
   a conical housing section which is arranged adjacent to the cylindrical housing section and which has the condensate discharge opening arranged therein.

8. The condensate separator as recited in claim 1, wherein a diameter of the gas entrance of the outlet port corresponds to a diameter of the upper base surface of the housing.

* * * * *